United States Patent
Twyford et al.

(10) Patent No.: US 9,737,711 B2
(45) Date of Patent: Aug. 22, 2017

(54) SYSTEM AND METHOD FOR SELECTIVE NEURAL ACTIVATION USING HIGH-FREQUENCY ELECTRICAL STIMULATION

(71) Applicants: Perry Twyford, Cambridge, MA (US); Changsi Cai, Braband (DK); Shelley Fried, Boston, MA (US)

(72) Inventors: Perry Twyford, Cambridge, MA (US); Changsi Cai, Braband (DK); Shelley Fried, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/893,549

(22) PCT Filed: May 23, 2014

(86) PCT No.: PCT/US2014/039314
§ 371 (c)(1),
(2) Date: Nov. 24, 2015

(87) PCT Pub. No.: WO2014/190245
PCT Pub. Date: Nov. 27, 2014

(65) Prior Publication Data
US 2016/0106981 A1    Apr. 21, 2016

Related U.S. Application Data

(60) Provisional application No. 61/827,170, filed on May 24, 2013, provisional application No. 61/841,869, filed on Jul. 1, 2013.

(51) Int. Cl.
*A61N 1/00* (2006.01)
*A61N 1/36* (2006.01)
(Continued)

(52) U.S. Cl.
CPC .......... *A61N 1/36046* (2013.01); *A61N 1/06* (2013.01); *A61N 1/36057* (2013.01); *G05B 15/02* (2013.01); *A61N 1/36139* (2013.01)

(58) Field of Classification Search
CPC .. A61N 1/06; A61N 1/36046; A61N 1/36057; A61N 1/36139; G05B 15/02
See application file for complete search history.

(56) References Cited

U.S. PATENT DOCUMENTS

| | | | |
|---|---|---|---|
| 4,408,608 A | 10/1983 | Daly et al. | |
| 8,626,306 B2 * | 1/2014 | Horsager | A61N 1/36046 607/54 |

(Continued)

OTHER PUBLICATIONS

International Search Report and Written Opinion under date of mailing of Oct. 16, 2014 in connection with PCT/US2014/39314.

(Continued)

*Primary Examiner* — George Manuel
(74) *Attorney, Agent, or Firm* — Quarles & Brady LLP (57) ABSTRACT

A system and method is provided for preferentially stimulating a portion of neural tissue including a first type of neurons and a second type of neurons. The method includes defining a waveform characterizing an electrical stimulus, wherein the waveform includes an amplitude-modulated wave of the electric stimulus. The method also includes applying the electrical stimulus having the defined waveform to a stimulating element located in proximity to the neural tissue to selectively activate the first type of neurons while leaving the second type of neurons one of substantially unaffected and suppressed in response to the electrical stimulus.

13 Claims, 7 Drawing Sheets

(51) Int. Cl.
*A61N 1/06* (2006.01)
*G05B 15/02* (2006.01)

(56) References Cited

U.S. PATENT DOCUMENTS

| | | |
|---|---|---|
| 2008/0058897 A1 | 3/2008 | McMahon et al. |
| 2011/0060410 A1 | 3/2011 | Tiedtke et al. |
| 2012/0035726 A1 | 2/2012 | Gross et al. |
| 2012/0083861 A1 | 4/2012 | Fried et al. |
| 2012/0277826 A1 | 11/2012 | Fried et al. |

OTHER PUBLICATIONS

Zaghloul, Ka et al., Different Circuits for CN and OFF Retainal Ganglion Cells Cause Different Contrast Sensitivities, the Journal of Neuroscience, Apr. 1, 2003; 23(7); pp. 2645-2648. figures 2-3, 7.

* cited by examiner

SYSTEM AND METHOD FOR SELECTIVE NEURAL ACTIVATION USING HIGH-FREQUENCY ELECTRICAL STIMULATION

CROSS-REFERENCE TO RELATED APPLICATIONS

This application represents the national stage entry of PCT International Application No. PCT/US2014/039314 filed May 23, 2014, which claims priority to and incorporates herein by reference U.S. Provisional Patent Application No. 61/841,869, filed Jul. 1, 2013, and U.S. Provisional Application Ser. No. 61/827,170, filed May 24, 2013, the contents of which are hereby incorporated by reference in their entirety for all purposes.

STATEMENT REGARDING FEDERALLY SPONSORED RESEARCH

This invention was made with government support under 1I01 RX000350-01A1 awarded by the VA Boston Healthcare System and 1 R01 EY019967 awarded by the National Institutes of Health. The government has certain rights in the invention.

BACKGROUND ART

The present disclosure relates to neural stimulation and, more particularly, to selective activation of targeted predetermined neurons through high-frequency electrical stimulation.

In the healthy retina, light is converted into very complex patterns of spatiotemporal signaling. Specifically, retinal ganglion cells (RGCs), the output neurons of the retina, generate complex patterns of action potentials that are carried to higher visual centers. There are different types of RGCs (at least twelve different types in the mammalian retina) and each type elicits a different pattern of action potentials to convey information. For example, some RGCs respond strongly to the onset of a light stimulus (referred to as ON cells) while others remain quiet when a light stimulus is turned on but respond strongly when the stimulus is turned off (referred to as OFF cells). Accordingly, many closely situated ganglion cells can each generate a different spiking response to a given stimulus simultaneously.

Outer retinal degenerative diseases such as age-related macular degeneration (AMD) and retinitis pigmentosa (RP) affect the vision of over a million people in the United States and many more worldwide. These diseases target the outer retina and typically result in the loss of function of the light-sensitive photoreceptors, thereby decreasing the light responsiveness of the eye. RGCs, as well as other neurons in the inner retina, are thought to survive the degenerative process and one of the key approaches in the field of retinal prosthetics is to optimize the way in which these surviving retinal neurons are stimulated.

There has been considerable progress in this field over the last decade, leading to the implementation of several clinical trials using retinal prosthetic devices. Some retinal prosthetics include arrays of stimulating electrodes positioned either at the inner or outer surface of the retina. Individual electrodes within the array are activated independently with the goal of creating meaningful patterns of spiking in the surviving neurons within the region around the electrode. Simultaneous activation of multiple electrodes is used to create percepts that have more complex spatial detail. Patients in these clinical trials have reported visual percepts arising from stimulation and some have even been able to perform simple tasks such as identifying household objects, performing limited navigation, and reading simple words. While this progress is highly encouraging, many aspects of overall performance remain somewhat limited. For example, even the fastest reading rates were restricted to only a few words per minute, and the average rate across all patients was much slower.

Although it is not entirely clear why device performance is limited, one likely factor is the use of suboptimal stimulation methods. For example, the acuity of normal vision is typically quite high because tightly-packed RGCs, especially in the fovea, each extract information from only a narrow portion of visual space. In contrast, the diameter of stimulating electrodes used in existing implanted devices can be up to 200 micrometers ($\mu$m). As a result, each electrode can stimulate tens or even hundreds of RGCs, thereby greatly reducing resolution. In addition, as described above, the retina contains different types of RGCs, such as ON cells and OFF cells, and each type extracts different features of the visual world and transmits this information to higher visual centers using distinct patterns of spiking. Ideally, a retinal prosthetic would replicate the above-described (natural) pattern of signaling, that is, separately activating the ON ganglion cells in a given patch of retina without simultaneously activating the OFF ganglion cells in the same region. However, due to the close proximity of different RGCs to one another, stimulation from any given electrode in existing prosthetic devices is likely to elicit spiking patterns in multiple RGC types simultaneously, thereby sending a signal to the brain that is non-physiological.

Recent work has shown some progress toward selective activation of RGC types. For example, a recent study used a multicapacitor array to hyperpolarize photoreceptor terminals, mimicking the physiological ON retinal response. However, targeting of photoreceptor terminals may limit the utility of such an approach due to photoreceptor degeneration in most patients that would be candidates for retinal prostheses. Similarly, another recent study was able to create differential responses in ON and OFF cells using sinusoidal stimulation. They too surmised that the ON/OFF differences were the result of photoreceptor activation (again limiting the utility of their approach). Yet another study found that ON cell populations in rabbit retina have lower stimulus thresholds than OFF cells in response to monophasic cathodal stimuli applied subretinally. These results did not extend to mouse retina however, raising questions as to its generality and therefore its suitability for clinical use.

Therefore, it would be desirable to provide a clinically useful device and methods capable of eliciting retinal response that better mimics physiological retinal output. New stimulation methods and devices that could provide more precise control over elicited neural activity, such as preferential targeting of specific RGC types, would bring the elicited retinal response more in line with physiological retinal output and, thus, lead to better clinical outcomes.

SUMMARY

An aspect of the present disclosure provides a method of preferentially stimulating a portion of neural tissue including a first type of neurons and a second type of neurons. The method includes defining a waveform characterizing an electrical stimulus, wherein the waveform includes an amplitude-modulated wave of the electric stimulus. The method also includes applying the electrical stimulus having the defined waveform to a stimulating element located in proximity to the neural tissue to selectively activate the first type of neurons while leaving the second type of neurons one of substantially unaffected and suppressed in response to the electrical stimulus.

Another aspect of the present disclosure provides a system configured to stimulate a neural tissue including a first type of neurons and a second type of neurons. The system includes a power source, a stimulating element powered by the power source and structured to be positioned in proximity to the neural tissue, and a controller in communication with the stimulating element. The controller includes a storage medium on which is stored program code such that, when the program code is executed by a processor, the program code causes the processor to define a waveform characterizing an electrical stimulus, wherein the waveform includes an amplitude-modulated wave of the electric stimulus, and control the stimulating element to apply the electrical stimulus having the defined waveform to selectively activate the first type of neurons while leaving the second type of neurons one of substantially unaffected and suppressed in response to the electrical stimulus.

Yet another aspect of the present disclosure provides a retinal prosthetic device including a power source, a stimulating element, a sensing element, and a controller. The stimulating element is powered by the power source and structured to be positioned in proximity to and apply stimulation to a plurality of retinal ganglion cells including a first type of retinal ganglion cells and a second type of retinal ganglion cells. The sensing element is powered by the power source and structured to receive a light stimulus in proximity to the plurality of retinal ganglion cells and to generate a light output representative of the light stimulus. The controller is in communication with the stimulating element and the sensing element and includes a storage medium on which is stored program code. When the program code is executed by a processor, the program code causes the processor to receive the light output from the sensing element, select pulse train parameters based on the light input, define a pulse train characterizing an electrical stimulus, the pulse train including the selected pulse train parameters, and control the stimulating element to apply the electrical stimulus having the defined pulse train to generate a first level of activity from the first type of retinal ganglion cells and a second level of activity from the second type of retinal ganglion cells.

BRIEF DESCRIPTION OF THE DRAWINGS

The invention will be more fully understood by referring to the following Detailed Description in conjunction with the Drawings.

DETAILED DESCRIPTION

In accordance with aspects of the present disclosure, methods and apparatus are disclosed for selective activation of targeted predetermined neurons through high-frequency electrical stimulation. Furthermore, with respect to activation of retinal ganglion cells (RGCs), by mapping physiological responses to stimuli for specific RGC types and correlating high-frequency stimulation parameters that specifically elicit such physiological responses, such methods and apparatus can be used in prosthetic devices to recreate some elements of normal retinal processing and, thus, lead to higher quality vision.

In accordance with one configuration, described with reference to FIG. 1, a system 10 is provided for selectively activating targeted neurons in neural tissue. The system 10 includes a power source 12, a controller 14, and a stimulating element 16. The power source 12 is enabled to power both the controller 14 and the stimulating element 16, and the controller 14 governs the operation of the stimulating element 16 to generate an output containing an electrical stimulus, as further described below. The power source 12 is connected to the controller 14 by connector 18. The power source 12 can be directly connected to the stimulating element 16 by a connector 20 or indirectly connected to the stimulating element 16 via the controller 14 by connectors 18 and 22. In addition, the controller 14 can communicate with the stimulating element 16 via the connector 22 or, in the alternative, through a wireless connection (such as an inductive coupling).

Figure 1:
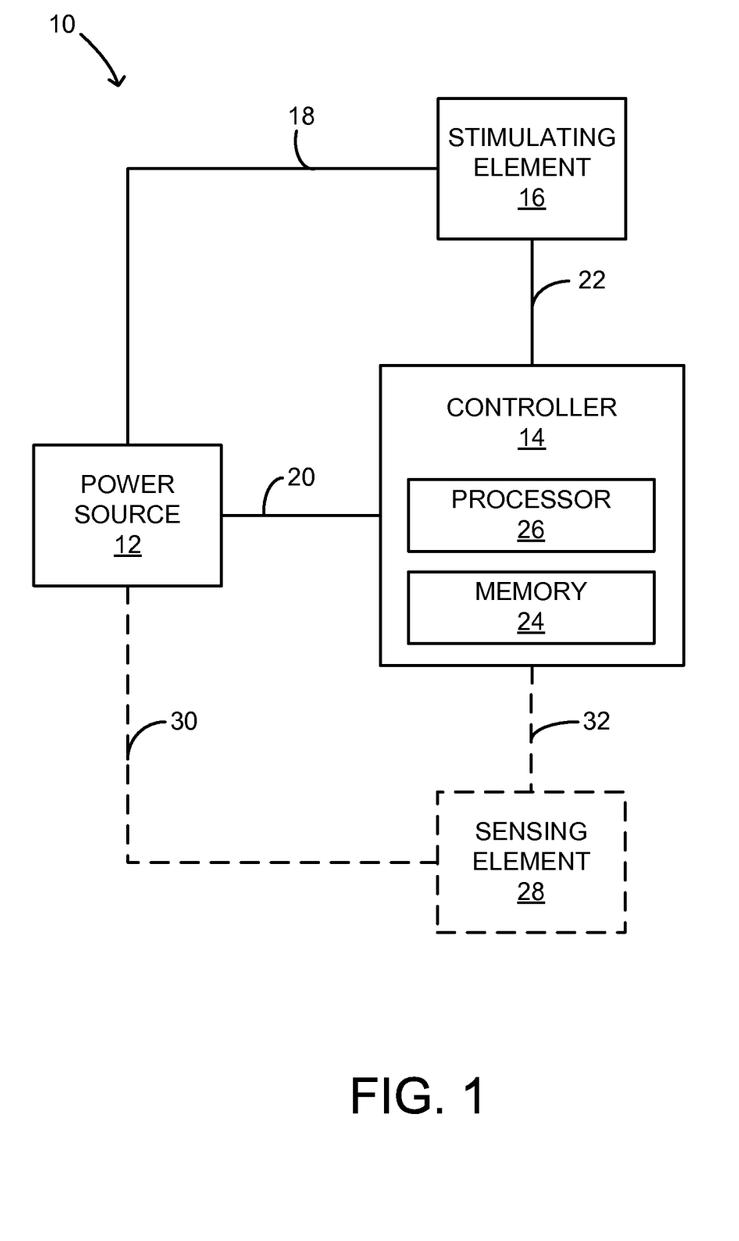
FIG. 1 is schematic illustration of a system according to aspects of the present disclosure.

With further reference to the stimulating element 16 of FIG. 1, the stimulating element 16 is structured to be positioned in proximity to a portion of neural tissue to permit application of an electrical stimulus to the neural tissue (that is, passing current from the stimulating element 16 to the neural tissue). The structure and configuration of the stimulating element 16 is dependent upon the application, that is, the type of neural tissue. For example, the stimulating element 16 can include one or more electrodes capable of individually applying or outputting an electrical stimulus. In some situations, such as applications related to stimulation of retinal tissue, the stimulating element 16 is configured as an electrode array. By way of example, a microphotodiode array (MPDA), as described by Zrenner et al., is a light sensitive 3.0×3.1 mm CMOS-chip with 1500 pixel-generating elements on a 20 um thick polyimide foil carrying an additional test field with 16 electrodes for direct electrical stimulation. (Zrenner, E, et al. 2011. "Subretinal electronic chips allow blind patients to read letters and combine them to words." Proc. R. Soc. B. 278, 1489-97.) In addition, in such applications, the stimulating element 16 is structured to directly stimulate retinal ganglion cells (RGCs) rather than, for example, photoreceptors or bipolar cells. Because RGCs are tightly packed within neural tissue, individual electrodes of the stimulating element 16 can span across tens or even hundreds of RGCs. As a result, the application of an electrical stimulus to the neural tissue from a single electrode causes application of the electrical stimulus to all of the RGCs in proximity of the single electrode.

With further reference to the controller 14 of FIG. 1, the controller 14 includes a storage medium 24 (that is, a tangible non-transitory and, optionally, computer-readable memory) and a processor 26. The storage medium 24 includes program code stored therein that governs operation of the processor 26 (that is, governs the processor 26 to execute certain process steps). Through execution of certain process steps governed by the program code, the processor 26 is operable to define a waveform characterizing the above-described electrical stimulus and control operation of the stimulating element 16 to apply the electrical stimulus. The waveform is defined to elicit specific patterns of activity from one or more types of neurons in the neural tissue when the electrical stimulus is applied to the neural tissue. In some situations, specific waveforms and/or waveform parameters can be stored in the storage medium 24 and retrieved by the processor 26. For example, waveform parameters are selected and retrieved by the processor 26 in order to define a specific waveform.

Generally, waveforms can include, but are not limited to, a single pulse, a train of pulses, triangular waveforms, sawtooth waveforms, sinusoidal waveforms, exponential waveforms, etc. Waveform parameters (or pulse train parameters) include frequency, waveform duration (pulse train duration), inter-pulse interval duration, amplitude, waveform shape, and/or amplitude modulation pattern, among others. In addition, the waveforms are biphasic, including a first cathodal/negative pulse followed by an equal and opposite anodal/positive pulse. Also, generally, the system 10 applies high-frequency stimulation (that is, frequencies above 1000 Hertz or 1000 pulses per second), in comparison to previous applications which limit frequencies to a few hundred pulses per second. Accordingly, the frequency parameter can be varied between about 1000 Hertz and about 100,000 Hertz, or higher.

As described above, with respect to retinal tissue, application of an electrical stimulus to the neural tissue from a single electrode causes application of the electrical stimulus to all of the RGCs in proximity of the single electrode. The purpose of stimulating the RGCs is to elicit a physiologically-accurate and, optionally, pre-characterized response by the RGCs. However, there are many types of RGCs in the retina (at least twelve in the mammalian retina). Types of RGCs include, for example, brisk transient (BT) cells (including ON-BT cells and OFF-BT cells), local edge detector (LED) cells, directionally selective (DS), cells, among others. In a healthy retina, each type of RGC extracts different features of the visual world and uses distinct patterns of action potentials to transmit these features to higher visual centers. Generally, different types of RGCs respond (that is, elicit action potentials in a specific spiking pattern) to light on, light off, light motion in a specific direction, etc. Thus, artificially eliciting similar action potential patterns in all RGCs in a given space through an electrical stimulus causes a non-physiological response.

In order to better mimic physiological response, waveforms are defined with waveform parameters to cause selective activation of targeted RGCs while suppressing or leaving other types of RGCs unaffected. In other words, a waveform is defined with waveform parameters to cause a first level of activity from a first type of RGCs and a second, different level of activity from a second type of RGCs simultaneously. The use of high-frequency stimulation, with additional specific parameters, allows for an identical stimulus to produce different responses in different RGC types. For example, a waveform including a specific, constant amplitude can generate a first baseline level of activity in one type of RGC and a second, different baseline level of activity in another type of RGC when applied to both types simultaneously. Baseline levels of activity are considered the natural activity or "noise" generated by RGCs, even at rest. In healthy cells, these levels vary for different cell-types. In another example, an amplitude-modulated waveform can selectively activate one type of RGC while suppressing or not affecting another type of RGC when applied to both types simultaneously. These examples are described in further detail below. Herein, activating an RGC can include increasing a rate of spiking (that is, action potentials elicited by the RGC), whereas suppressing an RGC can include decreasing a rate of spiking. Also, baseline levels of activity can include baseline spiking rates. By using high-frequency stimulation, in comparison to lower frequencies or single pulses applied in previous applications, spiking is not necessarily limited to one spike per pulse, but rather the purpose of this type of stimulation is to achieve specific activity levels (that is, spiking rates or patterns) elicited in response to stimulation. Furthermore, high-frequency stimulation allows for higher rates of activity at lower stimulus amplitudes, unlike lower frequencies. In addition, in response to an increase in amplitude, lower frequency stimulation elicits a monotonic response, wherein spiking rates only increase and then level off. In other words, as amplitude increases, spiking frequency increases until it levels off. Conversely, high-frequency stimulation elicits a non-monotonic response profile, wherein spiking rates increase, but then decrease as amplitude is further increased. This non-monotonic response, which is not seen at low frequencies, allows for eliciting preferential activity patterns in different types of neurons.

Referring back to the system of FIG. 1, in some configurations, the processor 26 is specifically programmed (that is, through the program code stored on the storage medium) to define a waveform, as described above, based on a desired and/or targeted physiological response. More specifically, the storage medium 24 includes a stored map or table of predetermined data that correlates a plurality of specific waveforms or specific waveform parameters to respective desired physiological responses (in essence, a "coding scheme" that relates artificial stimulation parameters to physiological responses). For example, these correlations are previously determined and mapped based on experimental data.

As an example, a desired physiological response may include a physiological response to having "lights on." When achieving such a response is required, the processor 26 retrieves or selects a specific waveform or waveform parameters correlated with this response in the map and applies an electrical stimulus characterized by this selected waveform to the neural tissue in order to elicit the desired physiological response. In other words, the processor 26 controls the stimulating element to apply the electrical stimulus to cause activation of targeted RGCs, in which activation of these targeted RGCs causes transmission of specific spiking patterns to higher visual centers that can interpret the spiking patterns as a "lights on" response.

In some configurations, the system 10 can be configured as part of a prosthetic device with the inclusion of a sensing element 28, as shown in FIG. 1. In such configurations, the power source 12 powers the sensing element 28 and can be directly connected to the sensing element 28 by a connector 30 or indirectly connected to the sensing element 28 via the controller 14 by connectors 18 and 32. The controller 14 communicates with the sensing element 28, via the connector 32, to receive a sensory output generated by the sensing element 28. The processor 26 processes these sensory outputs to determine a desired physiological response and controls operation of the stimulating element 18 as described above based on this desired physiological response. For example, another map correlating sensory inputs to desired physiological responses is stored within the storage medium 24. With respect to retinal prosthetic devices, the sensing element 28 is structured to be positioned in proximity to RGCs in order to sense light stimulus that would naturally be sensed by retinal tissue, and communicates visual outputs to the controller 14 representative of the sensed visual stimulus. In some configurations, the sensing element 28 can include, but is not limited to, an array of photo-sensitive devices or an image processing unit (such as a camera).

Figure 2:
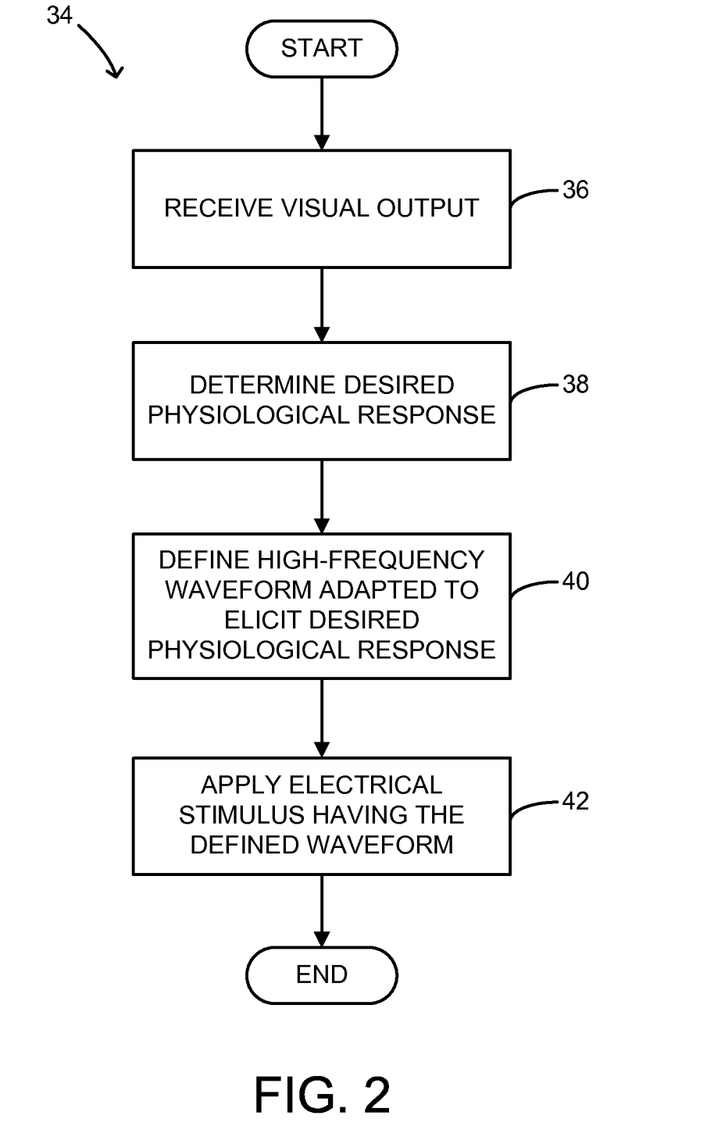
FIG. 2 is a flow chart setting forth a method according to aspects of the present disclosure.

In accordance with some configurations, described with reference to FIG. 2, a method 34 is provided for selective activation of targeted predetermined neurons through high-frequency electrical stimulation. The method 34 can be executed by the system of FIG. 1 or other suitable systems or prosthetic devices. As shown in FIG. 2, the method 34 generally includes receiving an output signal, such as a visual output, at process block 36 and determining a desired physiological response based on the visual output at process block 38. The method 34 also includes defining a waveform characterizing an electrical stimulus adapted to elicit the desired physiological response at process block 40 and applying the electrical stimulus having the defined waveform to a neural tissue to cause selective activation of targeted neurons of the neural tissue, thereby eliciting the desired physiological response, at process block 42.

In some configurations, with reference to process block 36, receiving the visual output can optionally be preceded by sensing a visual stimulus and transmitting the visual output representative of the visual stimulus. With reference to process block 38, determining the desired physiological response includes selecting the desired physiological response from predetermined data (such as a map or table) correlating physiological responses to visual outputs. With reference to process block 40, defining the waveform characterizing an electrical stimulus adapted to elicit the desired physiological response includes selecting the waveform and/or waveform parameters from predetermined data (such as a map or table) correlating waveforms to physiological responses. The waveform can be a high-frequency pulse train of a specific train duration, frequency, amplitude, and/or amplitude-modulation pattern. With further reference to process block 42, in some situations, selective activation of targeted neurons can include generating a first baseline activity level from a first type of neurons and simultaneously generating a second, different baseline activity from a second type of neurons. In other situations, selective activation of targeted neurons can include increasing an activity level of a first type of neurons while simultaneously not affecting or suppressing an activity level of a second type of neurons.

Figure 3:
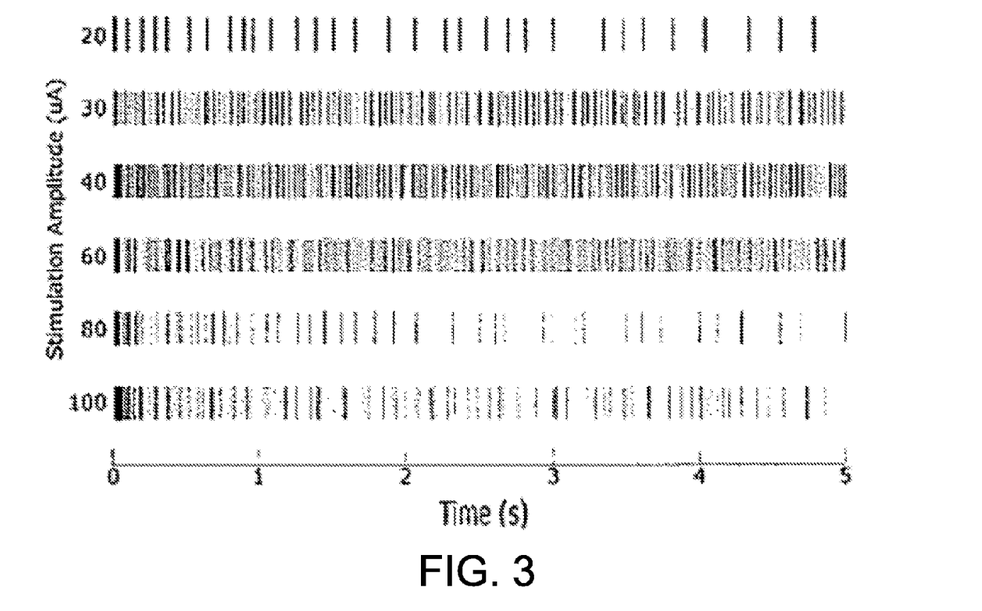
FIG. 3 is a graphical illustration of spiking activity of Brisk Transient retinal ganglion cells in response to high-frequency stimulation current of different amplitudes over time.

FIGS. 3-7 illustrate example high-frequency waveforms and specific waveform parameters empirically determined to selectively activate a targeted type of neurons when electrical stimuli having such waveforms are applied to the neural tissue. With specific reference to FIGS. 3 and 4, an experiment was conducted to observe responses from different types of RGCs when applying high-frequency stimulation at different amplitudes. FIG. 3 illustrates the response, that is, action potentials or spikes generated, from a brisk transient (BT) ganglion cell to a 5-second train of 2000-pulse per second, PPS, stimulation (that is, biphasic pulses, 100-microsecond phases, 160-microsecond cathodal-anodal inter-pulse interval, 140-microsecond anodal-cathodal inter-pulse interval) at amplitudes of 20 microamperes, 30 microamperes, 40 microamperes, 60 microamperes, 80 microamperes, and 100 microamperes. As shown in FIG. 3, though a response is elicited from stimulation at all amplitudes, the response of BT cells is highest at mid-level amplitudes (that is, 40-60 microamperes) and suppressed at higher amplitudes (that is, 80-100 microamperes).

Figure 4:
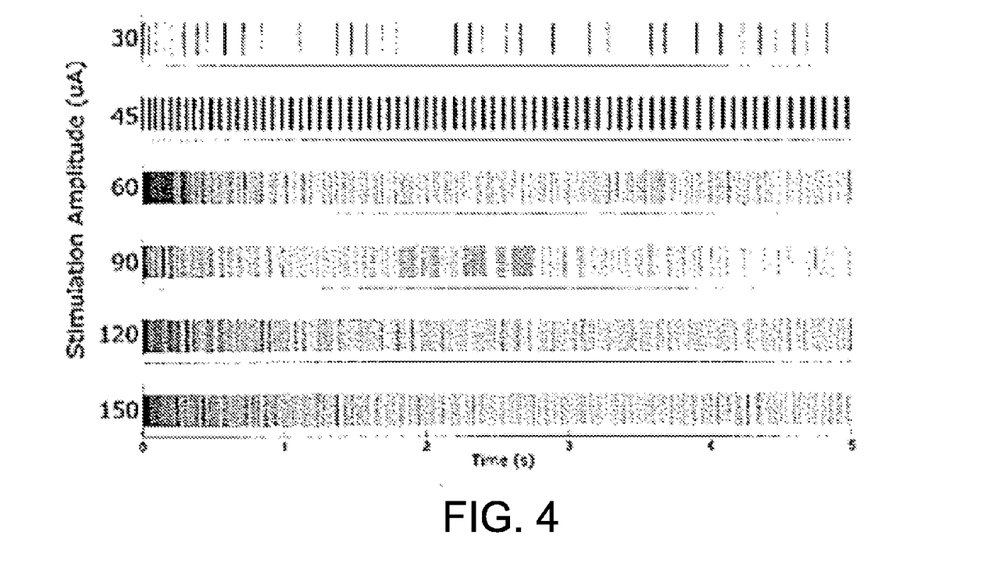
FIG. 4 is a graphical illustration of spiking activity of Directionally Selective retinal ganglion cells in response to high-frequency stimulation current of different amplitudes over time.
Figure 5:
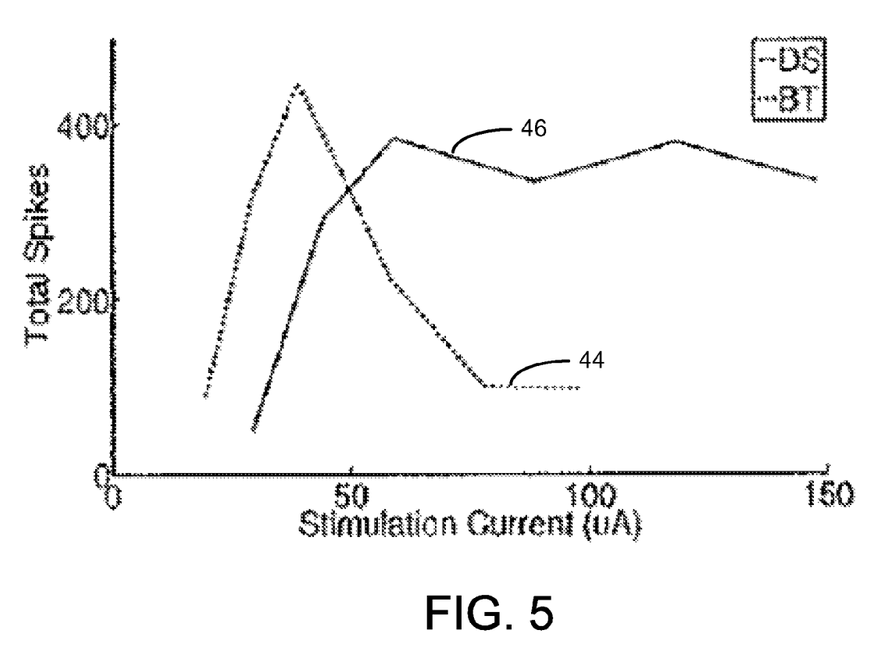
FIG. 5 is a graphical illustration of total spiking activity of Brisk Transient retinal ganglion cells and Directionally Selective retinal ganglion cells in response to high-frequency stimulation current of different amplitudes.

FIG. 4 illustrates the response from a directionally selective (DS) ganglion cell to a 5-second train of 2000 PPS stimulation at amplitudes of 30 microamperes, 45 microamperes, 60 microamperes, 90 microamperes, 120 microamperes, and 150 microamperes. In contrast to the results of FIG. 3, FIG. 4 illustrates that the response of DS cells is highest at higher amplitudes (that is, 60-150 microamperes). This difference in response between BT cells and DS cells is further illustrated in FIG. 5, where the total spikes elicited at each amplitude for both BT cells (line 44) and DS cells (line 46) over pulse train duration are plotted. In light of these results, a stimulus with a waveform including higher amplitudes can be applied to strongly activate, or increase spiking activity of, DS cells while only weakly activating, or decreasing spiking activity of, BT cells. Similarly, a waveform including lower amplitudes can be applied to strongly activate, or increase spiking activity of, BT cells while only weakly activating, or decreasing spiking activity of, DS cells. Thus, by selecting a specific amplitude in a high-frequency waveform, different types of RGCs can be preferentially activated while other types of RGCs are substantially unaffected or suppressed. Such a waveform can be selected to generate different baseline levels of activity from different types of RGCs, such as BT cells and DS cells. These results can be used as predetermined data correlating physiological responses to waveform parameters for use with the system 10 and method 34 described above.

Figure 6:
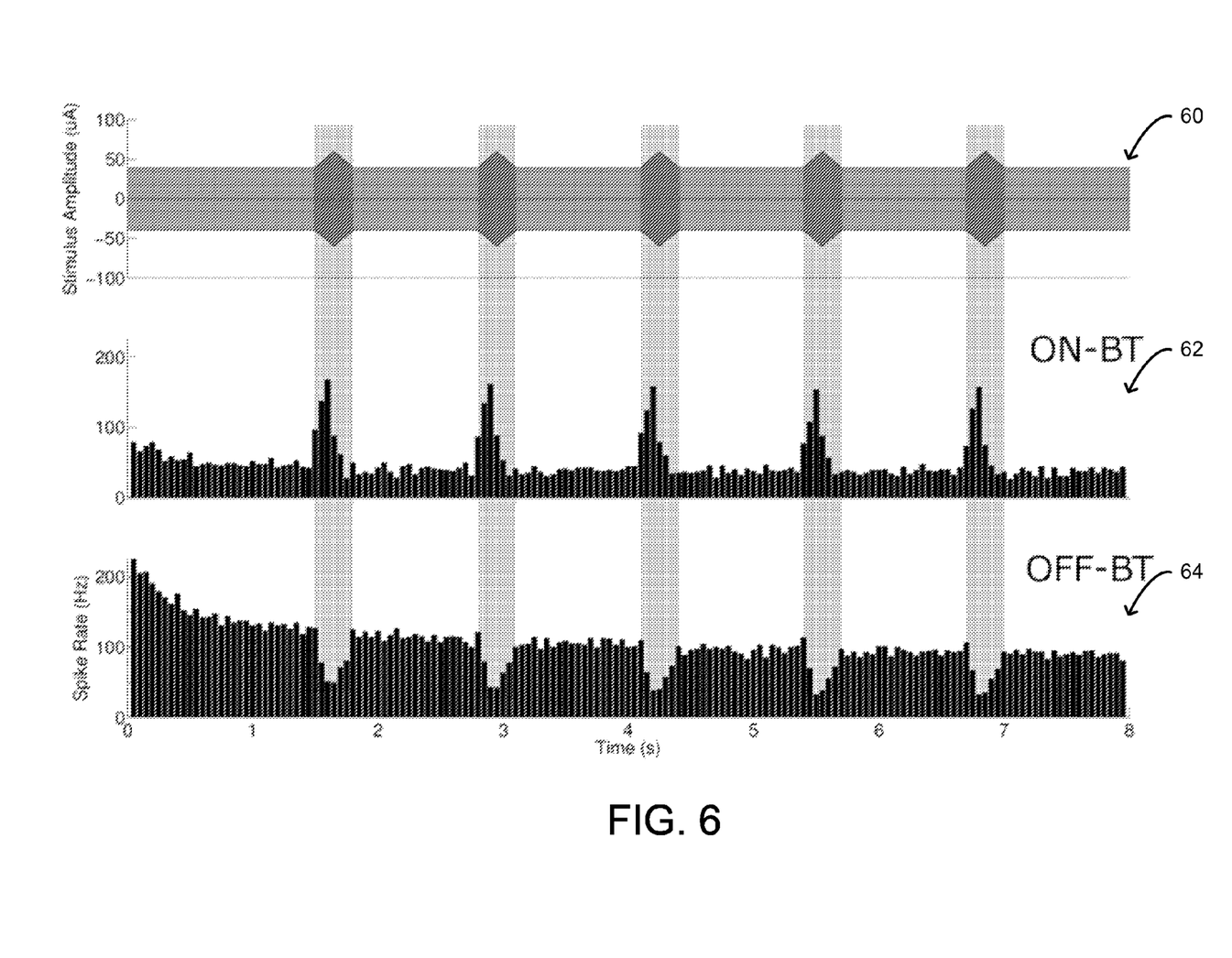
FIG. 6 is a graphical illustration of spiking activity of ON Brisk Transient retinal ganglion cells and OFF Brisk Transient retinal ganglion cells in response to an electrical stimulus having an amplitude-modulated, high-frequency waveform.
Figure 7:
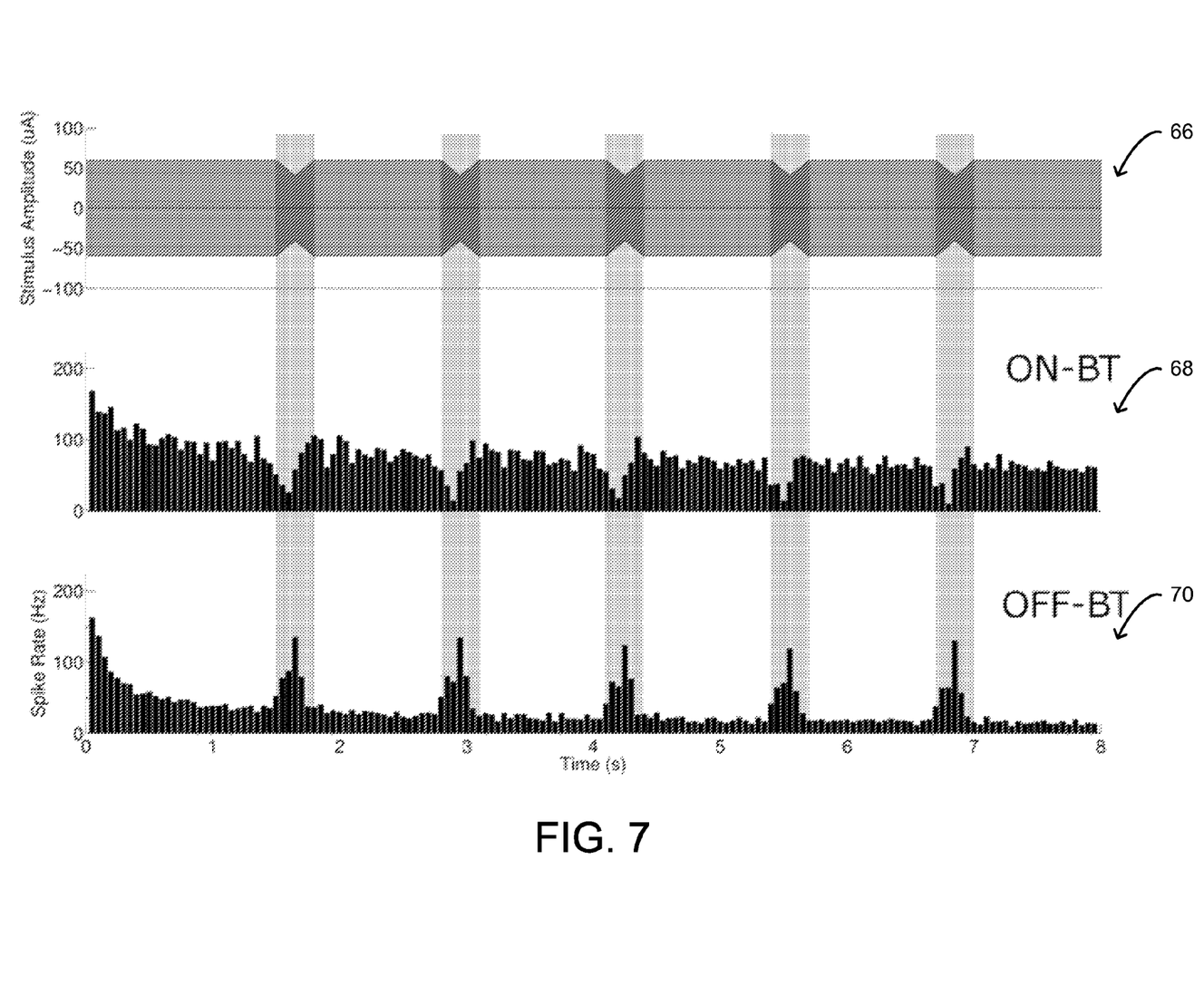
FIG. 7 is a graphical illustration of spiking activity of ON Brisk Transient retinal ganglion cells and OFF Brisk Transient retinal ganglion cells in response to another electrical stimulus having an amplitude-modulated, high-frequency waveform.
Figure 8:
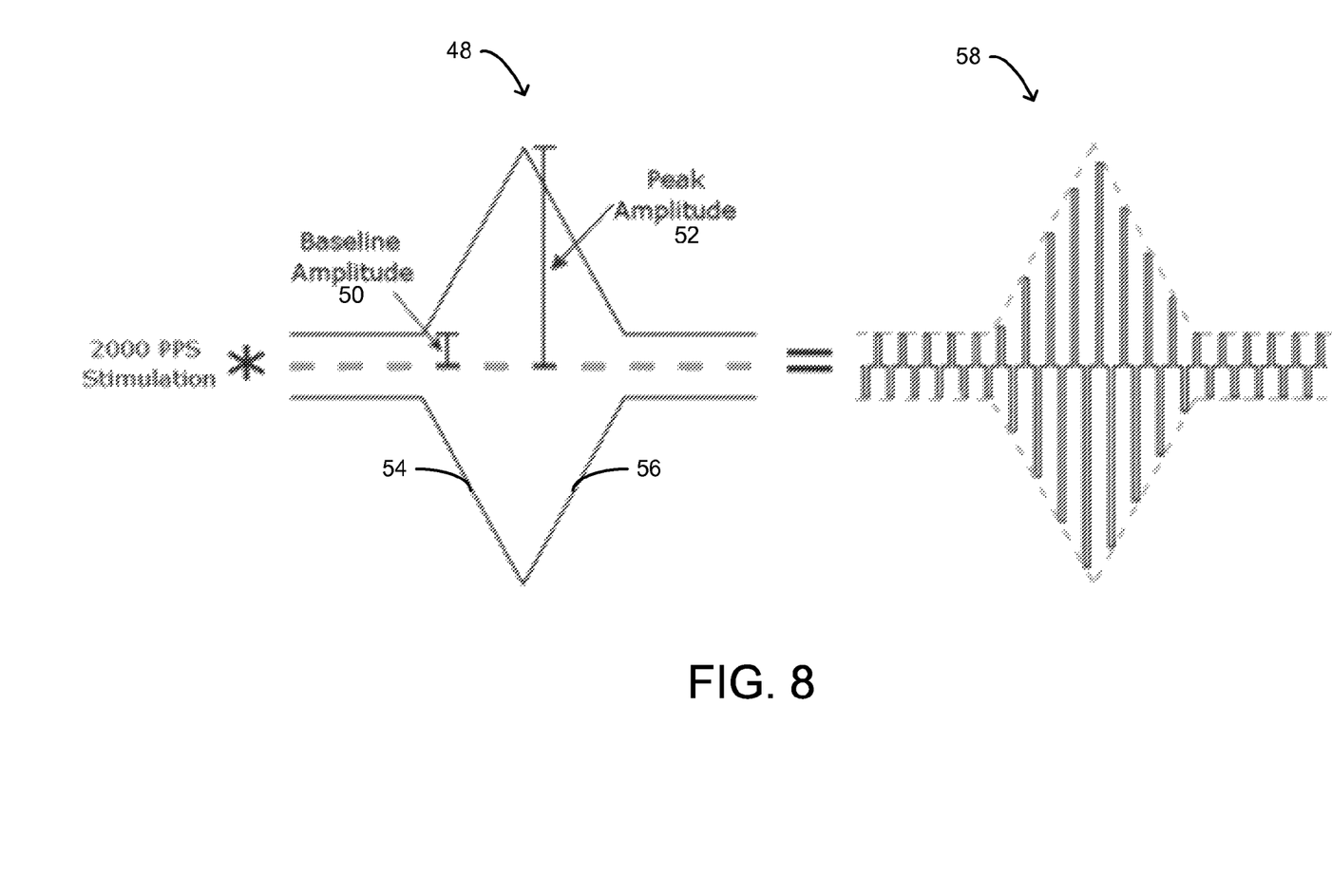
FIG. 8 is a graphical illustration of an amplitude-modulated waveform in accordance with aspects of the present disclosure.

With specific reference to FIGS. 6 and 7, an experiment was conducted to observe responses from different types of RGCs when applying amplitude-modulated high-frequency stimulation. More specifically, amplitude modulation of high-frequency stimulation was applied to achieve differential activation of ON BT cells versus OFF BT cells. FIG. 8 illustrates an example modulation envelope 48, as a diamond-shaped envelope with a base amplitude 50, a peak amplitude 52, a rising phase portion 54, and a falling phase portion 56, that can be applied to a continuous stimulation to achieve an amplitude-modulated waveform 58. FIG. 6 illustrates a waveform 60 including continuous 2000 PPS stimulus at a non-zero base amplitude, where the amplitude is periodically raised from the base amplitude to a higher peak amplitude and lowered back to the base amplitude (according to the diamond-shaped amplitude-modulation phase described above). The amplitude-modulation phase duration was 300 milliseconds (ms) in duration, including a 150 ms rising phase portion and a 150 ms falling phase portion. Five amplitude-modulation phases were repeated, with a 1-second interval between the end of a falling phase portion and the beginning of a subsequent rising phase portion. Response histograms with 50-millisecond bin size for ON-BT cells 62 and OFF-BT cells 64 are illustrated in FIG. 6 below the stimulation waveform. In response to a stimulus having this waveform, ON-BT cells 62 were shown to elicit a lower level of activity (that is, spiking activity in Hertz) when stimulated at the base amplitude, but increased in activity (that is, were more activated) during the amplitude-modulation phases. In contrast, OFF-BT cells 64 were shown to elicit a higher level of activity when stimulated at the base amplitude, but decreased in activity (that is, were suppressed) during the amplitude-modulation phases.

FIG. 7 illustrates a waveform 66 having a continuous 2000 PPS stimulus at a high amplitude (that is, a baseline amplitude), where the amplitude is periodically lowered from the baseline amplitude to a peak amplitude and raised back to the baseline amplitude (thus forming an inverse diamond-shaped amplitude-modulation pattern). A stimulus having this waveform 66 elicited an opposite response in comparison to the waveform 60 of FIG. 6. More specifically, OFF-BT cells 70 were shown to elicit a lower level of activity when stimulated at the baseline amplitude, but increased in activity (that is, were activated) during the amplitude-modulation phases. In contrast, ON-BT cells 68 were shown to elicit a higher level 2of activity when stimulated at the baseline amplitude, but decreased in activity (that is, were suppressed) during the amplitude-modulation phases. In these examples, the peak amplitude was 40 microamperes and the baseline amplitude was 60 microamperes.

The results illustrated in FIGS. 6 and 7 are similar to the differential response of such cells that occurs physiologically. Thus, by selecting an amplitude-modulated waveform with specific peak and non-zero baseline amplitudes, different types of RGCs are preferentially activated while other types of RGCs are substantially unaffected or are suppressed, thereby effectively mimicking a desired physiological response. The ability to selectively activate ON or OFF cells, as shown herein, can provide a much higher level of control than currently exists for many other neural prosthetic applications. Accordingly, these results can be used as predetermined data correlating physiological responses to waveform parameters for use with the system 10 and method 34 described above.

While specific values chosen for the above-described examples are given, it is to be understood that, within the scope of the disclosure, the values of all of parameters may vary over wide ranges to suit different applications and can be further optimized experimentally. For example, aspects of the disclosure contemplate stimulation frequencies from about 1000 Hz to about 100,000 Hz and amplitudes (that is, stimulation currents) from about 1 microampere to about 500 microamperes. Furthermore, additional predetermined data correlating other physiological responses to specific high-frequency waveforms can be applied in accordance with the present disclosure. For example, in addition to the diamond-shaped amplitude-modulation waveform described above, aspects of the disclosure contemplate other amplitude modulation shapes, such as sinusoidal and sawtooth, among others.

While the above systems and methods are described with specific reference to retinal tissues and retinal prostheses, these techniques can be applied in a wide range of other neural stimulation and neuroprosthesis applications, such as deep brain stimulation and prosthetics in the peripheral nervous system. Generally, the above systems and methods may be applied to any neural application involving heterogenous neural tissues (that is, where more than one type of neuron is present, wherein such neuron may be preferentially activated over another type of neuron). In addition, the above techniques can be applied to prosthetic retinas (that is, including prosthetic RGCs). In such applications, the prosthesis does not activate the RGCs, but rather takes the place of RGCs and applies artificial spiking patterns that correlate with desired physiological responses (for example, from predetermined, mapped data). These spiking patterns can then be transmitted to higher visual centers, which in turn can interpret the artificial spiking patterns as physiological responses of RGCs.

While the disclosure is described through the above-described exemplary configurations, it will be understood by those of ordinary skill in the art that modifications to, and variations of, the illustrated configurations may be made without departing from the inventive concepts disclosed herein. For example, although some aspects of the disclosure have been described with reference to a flowchart, those skilled in the art should readily appreciate that functions, operations, decisions, etc. of all or a portion of each block, or a combination of blocks, of the flowchart may be combined, separated into separate operations or performed in other orders. Moreover, while the configurations are described in connection with various illustrative data structures, one skilled in the art will recognize that the system may be configured using a variety of data structures. Furthermore, disclosed aspects, or portions of these aspects, may be combined in ways not listed above. Accordingly, the disclosure should not be viewed as being limited to the disclosed configurations.

What is claimed is:

1. A system configured to stimulate a neural tissue including a first type of neurons and a second type of neurons, the system comprising:
   a power source;
   a stimulating element powered by the power source, the stimulating element structured to be positioned in proximity to the neural tissue; and
   a controller in communication with the stimulating element, the controller including a storage medium on which is stored program code such that, when the program code is executed by a processor, the program code causes the processor to:
      define a waveform characterizing an electrical stimulus, the waveform including an amplitude-modulated wave of the electric stimulus, and
      control the stimulating element to apply the electrical stimulus having the defined waveform to selectively activate the first type of neurons while leaving the second type of neurons one of substantially unaffected and suppressed in response to the electrical stimulus.

2. The system of claim 1, wherein the waveform includes a frequency between about 1000 Hertz and about 100,000 Hz.

3. The system of claim 1, wherein the neural tissue is visual neural tissue and the neurons are retinal ganglion cells.

4. The system of claim 1, wherein the controller includes predetermined data stored in memory of the controller, wherein the predetermined data includes a map individually correlating a plurality of waveforms to a desired physiological response from the neural tissue.

5. The system of claim 4, wherein the plurality of waveforms vary in at least one of frequency, duration, amplitude, shape and amplitude modulation pattern.

6. The system of claim 4, wherein the processor is configured to select the waveform from the plurality of waveforms based on the desired physiological response.

7. The system of claim 1 and further comprising an electrical connector connecting the power source to the stimulating element.

8. The system of claim 1, wherein the stimulating element includes an array of stimulating electrodes.

9. A retinal prosthetic device comprising:
   a power source;
   a stimulating element powered by the power source, the stimulating element structured to be positioned in proximity to and apply stimulation to a plurality of retinal ganglion cells including a first type of retinal ganglion cells and a second type of retinal ganglion cells;
   a sensing element powered by the power source, the sensing element structured to receive a light stimulus in proximity to the plurality of retinal ganglion cells and to generate a light output representative of the light stimulus; and
   a controller in communication with the stimulating element and the sensing element, the controller including a storage medium on which is stored program code such that, when the program code is executed by a processor, the program code causes the processor to:
   receive the light output from the sensing element,
   select pulse train parameters based on the light input,
   define a pulse train characterizing an electrical stimulus, the pulse train including the selected pulse train parameters and forming an amplitude-modulated wave of the electric stimulus, and
   control the stimulating element to apply the electrical stimulus having the defined pulse train to generate a first level of activity from the first type of retinal ganglion cells and a second level of activity from the second type of retinal ganglion cells.

10. The device of claim 9, wherein the pulse train parameters include a frequency between about 1000 pulses per second and about 100,000 pulses per second.

11. The device of claim 9, wherein the amplitude-modulated pulse train and the first level of activity includes an increased spiking rate from a baseline spiking rate of the first type of retinal ganglion cells and the second level of activity includes a decreased spiking rate from a baseline spiking rate of the second type of retinal ganglion cells.

12. The device of claim 9, wherein the pulse train is a constant-amplitude biphasic pulse train and the first level of activity includes a first baseline spiking rate and the second level of activity includes a second, different baseline spiking rate.

13. The device of claim 9, wherein the controller includes predetermined data stored in memory of the controller, wherein the predetermined data includes a map individually correlating the pulse train parameters to a physiological response from the plurality of retinal ganglion cells to the light stimulus.

* * * * *

UNITED STATES PATENT AND TRADEMARK OFFICE
CERTIFICATE OF CORRECTION

PATENT NO. : 9,737,711 B2
APPLICATION NO. : 14/893549
DATED : August 22, 2017
INVENTOR(S) : Perry Twyford et al.

Page 1 of 1

It is certified that error appears in the above-identified patent and that said Letters Patent is hereby corrected as shown below:

In the Specification

Column 9, Line 22, "2of" should be --of--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*